United States Patent [19]

Alt

[11] Patent Number: 5,009,234
[45] Date of Patent: Apr. 23, 1991

[54] FOR THE THERMODILUTION METHOD OF DETERMINING CARDIAC OUTPUT

[76] Inventor: Eckhard Alt, Eichendorffstrasse 52, 8012 Ottobrunn, Fed. Rep. of Germany

[21] Appl. No.: 301,760
[22] PCT Filed: Apr. 27, 1988
[86] PCT No.: PCT/DE88/00240
   § 371 Date: Dec. 22, 1988
   § 102(e) Date: Dec. 22, 1988
[87] PCT Pub. No.: WO88/08274
   PCT Pub. Date: Nov. 3, 1988

[30] Foreign Application Priority Data

Apr. 27, 1987 [DE] Fed. Rep. of Germany ....... 3714027

[51] Int. Cl.$^5$ .............................................. A61B 5/02
[52] U.S. Cl. .................. 128/672; 128/692; 128/736
[58] Field of Search ................ 128/691–692, 128/736, 713, 672–675, 748, 341, 344

[56] References Cited

U.S. PATENT DOCUMENTS

| | | | |
|---|---|---|---|
| 3,446,073 | 5/1969 | Auphan et al. | |
| 3,726,269 | 4/1973 | Webster, Jr. | |
| 3,733,899 | 5/1973 | Auphan et al. | 128/692 X |
| 4,508,103 | 4/1985 | Calisi | 128/673 |
| 4,543,961 | 10/1985 | Brown | 128/667 |
| 4,587,975 | 5/1986 | Salo et al. | 128/693 |
| 4,595,015 | 6/1986 | Jansen et al. | 129/692 X |
| 4,621,646 | 11/1986 | Bryant | 128/692 |
| 4,632,125 | 12/1986 | Webler et al. | 128/736 X |
| 4,718,423 | 1/1988 | Willis et al. | 128/634 |
| 4,730,623 | 3/1988 | Lee | 128/736 X |
| 4,777,951 | 10/1988 | Cribier et al. | 128/748 X |
| 4,796,640 | 1/1989 | Webler | 128/736 |

OTHER PUBLICATIONS

Michael J. Ackerman, Ph.D., Computer Applications in Medical Care, Nov. 10–Nov. 13, Baltimore, pp. 41–44.

Primary Examiner—Kyle L. Howell
Assistant Examiner—John P. Lacyk
Attorney, Agent, or Firm—Laurence R. Brown

[57] ABSTRACT

This invention relates to a catheter (1) and accompanying system for diagnosis of the cardio-vascular system of a patient. The catheter (1) flexible tube body (2), having at least one channel (3) therethrough leading from the extracorporal proximal end to the distal area having a fluid discharge opening (6) is introduced into preformed vessels (31) of the body to extend into the heart for measuring physical parameters representative of the cardiac condition of the patient. A temperature sensor (8) is disposed on the catheter toward the proximal end with respect to the opening (6) at the distal end to allow for diagnostic and interventional measures to be taken in the left heart. Between the opening (6) and the sensor (8) may be disposed a dilatation balloon (7) inflatable from the outside. Also, it is advantageous to provide a second temperature sensor (17) in the area of the distal openings (6) as well as a further opening (21) in the area of the first temperature sensor. An external instrument (34) is used to evaluate and display the physical values determined from the catheter sensors for determination of the cardiac condition of the patient. This single catheter located in the left heart thus provides all the data necessary for analysis of the cardiac performance that heretofore required two separate insertions of a catheter.

22 Claims, 4 Drawing Sheets

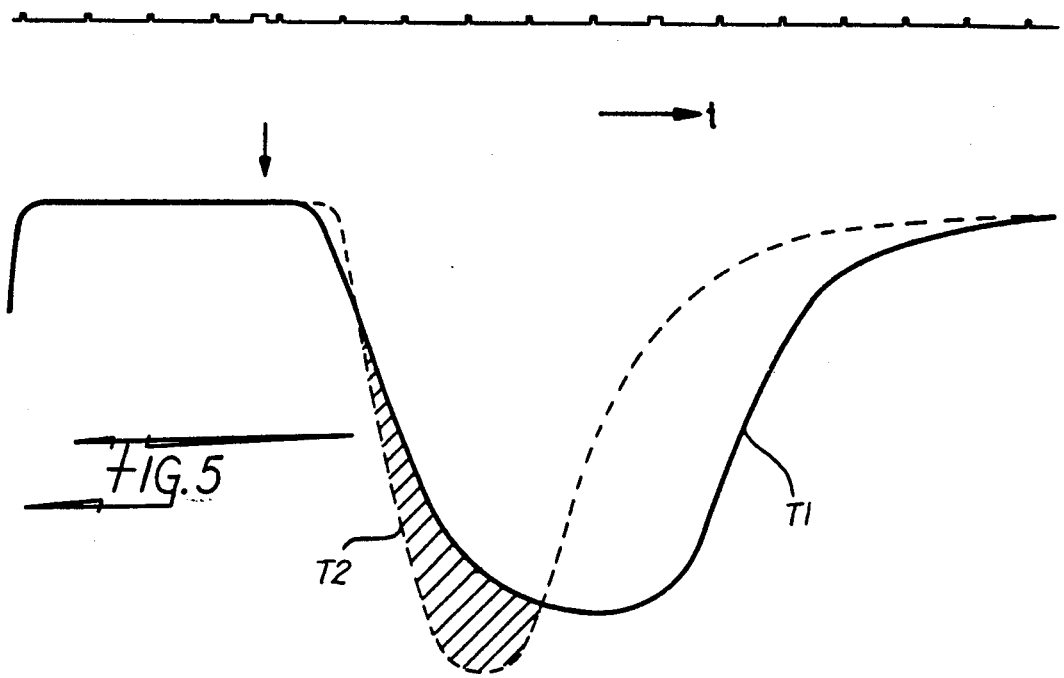
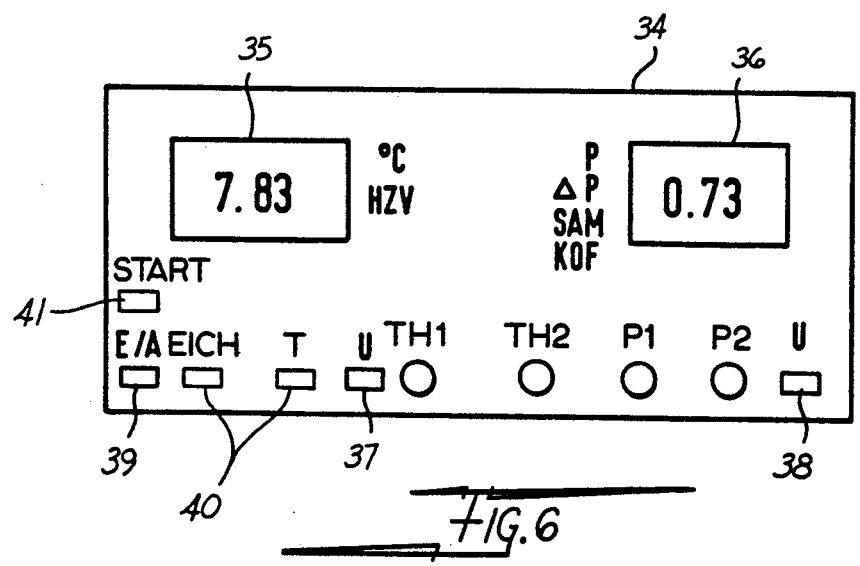

FOR THE THERMODILUTION METHOD OF DETERMINING CARDIAC OUTPUT

FIELD OF THE INVENTION

This invention relates to catheter systems for monitoring the condition of a patient's heart, and more particularly it relates to such catheter systems operable with the thermodilution method of determining cardiac output.

BACKGROUND OF THE INVENTION

Catheters to be introduced into the human body have been known for many years. The first description of such a catheter for probing the heart is from W. Forssmann and appeared in Klinische Wochenschrift 8, 1929, pp. 2085 ff. A great variety of experience has been gathered with such catheters in the area of diagnostics. A survey of the catheters used and the diagnostic measures to be performed therewith can be found in the company publication Hewlett-Packard Application Note 762 "A Guide to Hemodynamic Monitoring using the Swan-Ganz Catheter", 1978. As of the seventies, catheters with so-called dilatation balloons have also been used. Such balloons are inflatable from the outside and serve to widen congenital or acquired narrowings (stenoses) in the human vascular system. See for example A. Cribier et al., "Percutaneous Transluminal Balloon Valvuloplasty of Adult Aortic Stenosis": Report of 92 cases, published in JACC Vol., No. 2, Feb. 1987, pp. 381 ff.

One diagnostic measure, for example, is to take hydrostatic pressure measurements with one catheter having a plurality of separate channels and a plurality of lumina, a so-called multilumen catheter. The individual channels are directed toward the exatracorporal proximal end of the catheter and may be connected via standardized connections to pressure sensors for measuring the hydrostatic pressures at the lumen openings of the individual channels and the pressure difference or pressure gradient. Such a catheter may also be provided additionally with a temperature sensor, e.g. a small thermistor, for taking measurements of the cardiac pumping behavior, i.e. measurements of the cardiac output, by a so-called thermodilution method. By this method, according to the prior art, a cryogen solution is injected from the proximal end of the catheter via a channel into the blood vessel, e.g. the right ventricle of the heart, which solution after a certain time flows past the temperature sensor located toward the distal end. The temperature drop at the temperature sensor location as a function of the flow time of the cryogen solution in the blood circulation can then be used to determine the cardiac output, as set forth for example in U. S. Pat. Nos. 4,502,488 and 4,105,022. The connections of the temperature sensor are directed in the catheter tube to the proximal end and are connected there via standardized connections with a microcomputer, which directly states the required measured values, such as the cardiac output in liters per minute. Such measurements up to now have been taken primarily only in the right heart, with the catheter being pushed through a vein into the right heart or the pulmonary circulation.

A typical case of routine application of such a right heart and pulmonary cardiac output measuring catheter is with a patient having a previous myocardial infarction or some type of cardiomyopathy and therefore reduced pumping function of the heart. In such a patient a typical procedure is to apply a left ventricular angiography catheter and to inject dye into the left ventricle and by means of X rays to determine the contraction pattern of this left ventricle. It is described as ejection fraction indicating how much of the percentage of the ventricular volume is ejected by one heart beat. In addition to this indicator of the overall ventricular function, routinely now a second catheter is put into the venous and right heart system of the patient in order to measure cardiac output by the conventional way described above to thereby determine the overall pumping function of the heart in liters of blood pumped per minute. Of special interest also is the knowledge of cardiac output in diagnosing the degree of severeness of valvular stenosis or regurgitation. The prior art required the use of two catheters, one in the right heart to measure cardiac output and one in the left heart to measure pressure and ejection fraction.

One condition for the measurement of heart output in the left heart by the thermal dilution effect is that the direction of blood flow and the direction of the injected cryogenic solution is opposite. This has been identified as a problem in U.S. Pat. No. 3,726,269 W. Webster, Jr. Apr. 10, 1973 to be solved by providing two different temperature sensors placed respectively in the blood flow and the cryogenic solution flow paths for measuring coolant and dilution temperatures separately, This technique requires one temperature sensor to be located within the catheter and the other to be located outside the catheter in the blood flow path being diluted by the cryogenic solution. Thus the design and placement of the two required temperature sensors critically restricts the location and construction of the catheter. In particular, for each temperature measurement this technique requires placement of separate wires to multiple temperature sensors, and special construction for extending wires through the catheter walls. Also determination of the significant temperature from which cardiac output may be determined with two such sensors is limited to the temperature at a single point in the blood flow path, namely the position of the sensor located outside the catheter. Accordingly even though there are two temperature sensors, the catheter would have to be moved about to determine the blood temperature at two significantly different positions in the cardiovascular system of the patient. This prior art temperature system is limited to the determination of the cardiac output and the ventricular volume. The latter critically relates to peak thermal amplitudes, a function of the injection rate of the cryogenic solution, which is usually manually controlled and thus not subject to precise rate control.

Also the prior art thermodilution technique presents problems in the detection of cardiac output from the temperature measurements with two thermal sensors, in that the measurements are critical to a fixed rate of injection of the cryogenic solution to provide steady state temperatures for analysis. This problem is recognized for example in an article of R. B. Dew entitled "Personal Computer System for Automatic Coronary Venous Flow Measurement" on pp 41–44 of the Proceedings, The Ninth Annual Symposium on Computer Applications in Medical Care, Nov. 10-13, 1985. Such a fixed injection rate is not readily attained in conventional catheters with cryogenic solutions administered manually in impulse fashion.

Introducible catheters are used not only for diagnostic data gathering, but also increasingly for performing therapeutic measures in the circulatory system. These invasive but nonoperative measures shall be explained with reference to the dilatation of a cardiac valve stenosis also described in the above-mentioned essay by Cribier et al. First a dilation catheter with a dilatation balloon is pushed beyond the narrowing, e.g. a stenosis of an aortic valve, the uninflated balloon being located in the stenosis area. With the aid of a channel leading to the proximal end within the catheter tube having a lumen before the dilatation balloon, the pressure before the stenosis, the prestenotic pressure, is now measured hydrostatically. Then, according to prior art, the blood pressure after the stenosis, the poststenotic pressure, is measured in the same way with the aid of a second arterial catheter.

Finally, a thermodilution catheter is introduced into the pulmonary artery, i.e., right heart and pulmonary circulation, via a vein. A predefined amount of a cryogen solution is then injected, as described above, into a proximal opening of this thermodilution catheter, which also has a distal temperature sensor, and the temperature gradient in time at the distal location of the temperature sensor is measured. The cardiac output is determined therefrom. The measured values determined with the individual catheters are fed separately to a computer. According to Gorlin's formula, the area KOF of a cardiac valve opening is directly proportional to the volume of blood $V_{eff}$ flowing through the valve per unit of time and inversely proportional to the root of the pressure gradient $\_P_m$ across the constricted valve:

$$KOF = \frac{V_{eff}}{44.5 \cdot K \cdot \sqrt{\_Pm}} \, [cm^2]$$

To calculate the extent of a stenosis or ascertain the success of distending the stenosis with the aid of so-called balloon dilatation, one must therefore not only determine the pre- and post stenotic pressure and thus the pressure gradient, but also the time intervals in which the blood flows through the narrowing as well as the amount of blood flowing through. This then can be used to determine the actual cardiac valve area. It does not suffice merely to measure the pressure gradient, since manipulations of arteries when introducing the catheter and the pressure on the blood vessel at the point of introduction often bring about a vegetatively induced change in the cardiac pumping amount, the heart rate and thus the cardiac output. Even with the same stenosis, different pressure gradients arise in accordance with the flowing amount of blood, so that as a rule several measurements must be taken to determine the cardiac output, generally two to three, in particular when the patient has a fluctuating cardiac output.

Only when reliable measured values are obtained is the dilatation balloon inflated in order to distend the stenosis.

The described process is time consuming. In particular when the measured values are being fed to the evaluating computer and during the evaluation time, all further activities are blocked. Evaluation generally takes two to four minutes. In particular the time factor is a risk for the patient. Thus, the inserted catheter may move out of its position or even fall out. There is also a danger of thrombo-embolism. Dysrhythmia can also occur which may be triggered, for example, directly by the mechanical contact of the catheter with the heart muscle. The necessary long dwell time of the catheter may also lead to a loss of blood at the point of introduction of the catheter, which again alters the cardiac pumping behavior. The introduction of a plurality of catheters is also very unpleasant for the patient. When the measured values are finally available, a measurement must be taken once again after dilatation of the stenosis in order to verify whether the stenosis has actually been distended to the desired extent.

DISCLOSURE OF THE INVENTION

This invention corrects the prior art problems and provides a catheter and catheter instrument system more easily taking measurements for diagnosis of cardiac conditions. In particular pressure measurements are analyzed as well as cardiac output using the thermodilution method. A single catheter is adapted for comprehensive applications with a single insertion, preferably in the left heart. In particular quick and efficient diagnosis and treatment is now feasible for therapeutically distending narrowings with a single insertion of the catheter. The catheter is a multipurpose instrument for diagnosis of the foregoing various cardiac conditions, for treatment of stenosis, and for determining the dynamic condition of the heart muscle by dye injection along with XRay motion picture analysis.

Thus a preferred catheter embodiment has at least one channel with a lumen and a temperature sensor, e.g. a thermistor, in reversed order along the catheter as compared with the prior art catheters for cardiac output measurements within the right heart. The lumen provided for the injection of the cryogen, or a plurality of lumina located beside one another for better mixture of the cryogen with the bloodstream, is preferably located at the distal end, this distal end being preferably bent. The temperature sensor is located toward the proximal end of the catheter. This catheter permits direct measurements in the left heart, such as pressure measurement and cardiac output measurements by the thermodilution method.

When a cryogen is injected it first flows within the catheter past the temperature sensor before leaving the lumen at the distal end of the catheter, thereby cooling the temperature sensor. After leaving the lumen, however, the cryogen is conducted back toward the temperature sensor through the flow of blood, so that the degree of cooling due to the returning blood flowing past and the resulting temperature gradient can be measured there. It has turned out that in spite of the primary cooling of the thermistor by the cryogen flowing past, the subsequent measurements for determining the systolic discharge time and discharge amount and the cardiac output can be taken from a single thermal sensor within the cryogen flow path with a precision which is not inferior to the precision heretofore achieved by a right heart dilution method in which the temperature sensor was not primarily cooled by the cryogen flowing past in the catheter.

To distend narrowings in the vascular system, the catheter may also be provided with a dilatation balloon. According to this invention, the catheter then has at the same time means for determining the cardiac output as well as means on each side of the dilatation balloon for determining the pre- and post-stenotic blood pressure. The cardiac output can be determined by different methods, for example by injecting a thermal solution as in U.S. Pat. No. 4,217,910 or by measuring the impedance change after injecting a saline solution as in U.S. Pat. No. 4,572,206.

A simple method, however, is the above-mentioned thermodilution method. To determine the pre and post-stenotic blood pressure, pressure sensors are also possible using semiconductors. However, the blood pressure is advantageously measured hydrostatically at one opening located before and one after the dilatation balloon which each communicate with a channel leading to the extracorporal proximal end of the catheter. This makes it possible for the first time to eliminate, for example, a stenosis of the aortic valve in the left heart with the aid of only one catheter, which also is used to determine the measured values necessary for this intervention. This drastically reduces the time required for evaluating the measured values and for the therapeutic measure as compared with the conventional method, thereby also diminishing noticeably the above mentioned risks for the patient. Further, the use of only one catheter instead of three as required up to now, clearly reduces the discomfort of the patient.

Due to the simultaneous measurement of the pressure gradient, systolic discharge time, heart rate and cardiac output made possible by this catheter, the therapeutic measures can also be validated immediately by the available measured values to immediately determine the cardiac output and the area of opening of the stenosis calculated therefrom. Optionally, the average pressure gradient can also be stated. The physician thus constantly has a good grasp of the course of his interventions.

Further embodiments, features and advantages of this invention can be found throughout the following description, claims and drawings.

BRIEF DESCRIPTION OF THE DRAWINGS

The invention shall be explained in more detail in an embodiment with reference to the drawings, in which:

FIG. 5 shows temperature curves from temperature sensors in a dilution diagnosis with the catheter afforded by this invention, FIG. 6 shows a schematic view of a small computer with readout display devices operable together with the catheter of this invention for processing data useful in the diagnosis of the cardiac condition.

THE PREFERRED EMBODIMENTS

Figure 1:
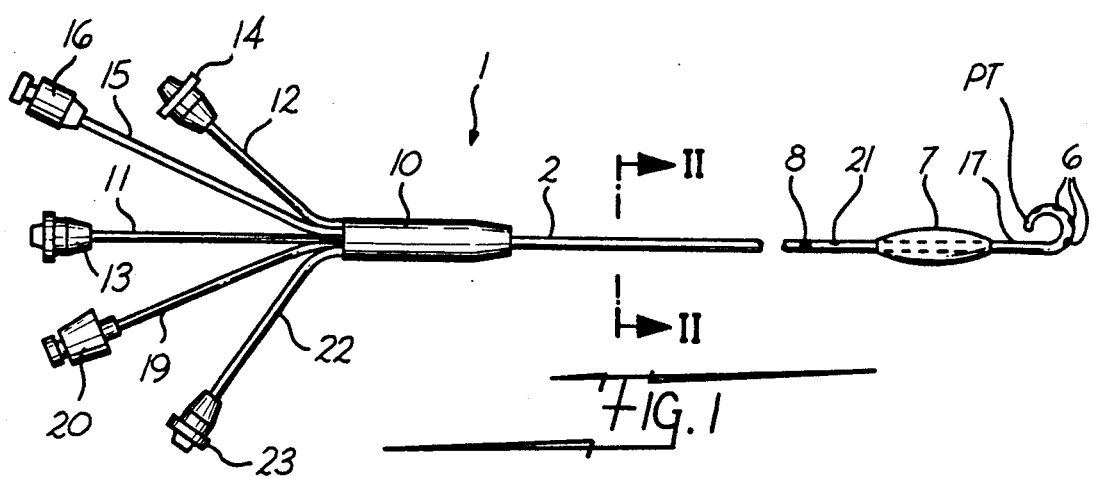
FIG. 1 shows a catheter of this invention useful as a dilatation catheter.
Figure 2:
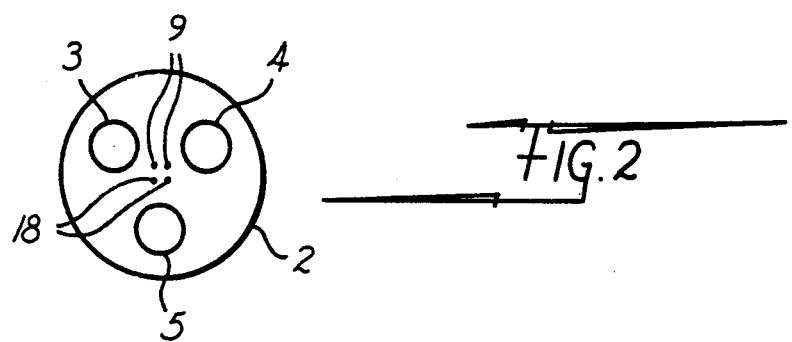
FIG. 2 shows a cross-section sketch taken along II—II in FIG. 1.
Figure 3:
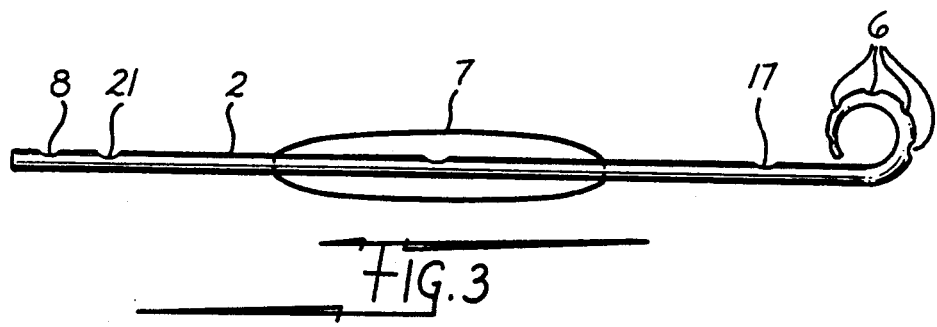
FIG. 3 shows an enlarged view of the distal area of the dilatation catheter.

In FIG. 1 the dilatation catheter 1 afforded by this invention is shown. This catheter 1 comprises an elastic tube 2 having three hollow channels 3, 4, and 5. At the distal end PT the tube is bent into a circular shape (pigtail). In this area there are a plurality of communicating openings, so-called lumina 6, which communicate with channel 3. Toward the proximal end of the catheter 1 there is a dilatation balloon 7 which can be inflated via channel 4. Further on toward the proximal end there is a thermistor 8 whose conducting wires are directly in the center of tube 2. Channels 3 and 4 are continued after a proximal connection block 10 in separate conduits 11 and 12, each provided at the end with a standardized joint piece 13, 14. Via a check valve at 14, dilatation balloon 7 may be inflated by a syringe. Via joint piece 13 cryogen can be sent through the catheter to leave at openings 6. This piece may be connected with a pressure sensor for measuring the blood pressure at lumina 6 hydrostatically. Conduits 9 and thermistor 8 are united in a cable 15 which opens into a standard connection 16. In this connection 16 there in also a line-up bridge circuit for thermistor 8.

In addition the catheter may have in the distal area between distal end PT and dilatation balloon 7 a further thermistor 17 whose connecting wires 18 are conducted separately inside tube 2 and united at the proximal end to form a cable 19 with a corresponding connection 20. Connection 20 is constructed like connection 16 and thus again has a line-up circuit. In the vicinity of first thermistor 8 there is a further opening 21 which communicates with channel 5 in tube 2 and opens after proximal end piece 10 into a conduit 22 with a joint piece 23.

Figure 4:
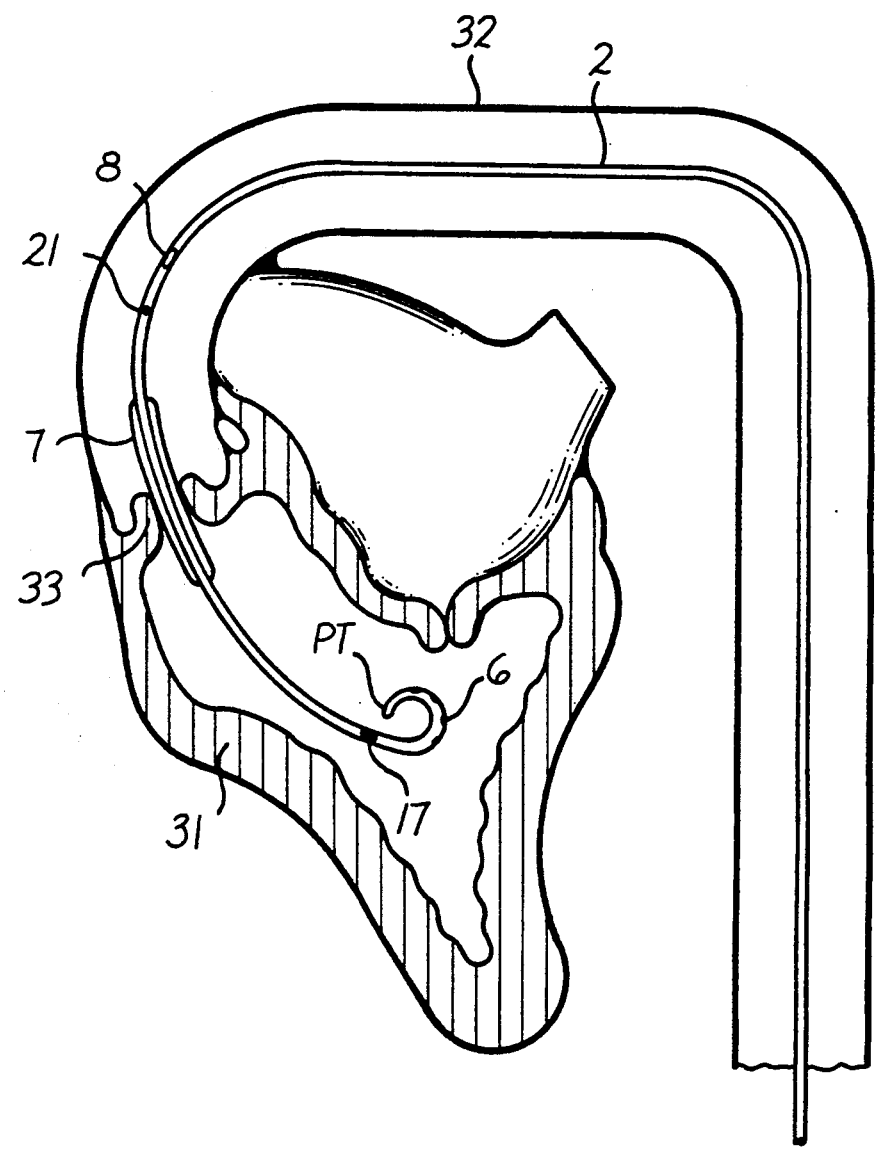
FIG. 4 schematically shows the position of the dilatation catheter of FIG. 1 in the aorta and the left heart.

FIG. 4 shows the position of the catheter in the left heart 31. Tube 2 of the catheter is inserted via the aorta into the left heart in such a way that the distal curved end PT of the tube is located in the left ventricle and dilatation balloon 7 in the area of aortic valve 33. This arrangement is to serve, for example, to eliminate a stenosis of the aortic valve. In this position, openings 6 and thermistor 17 are thus located in the left ventricle. Thermistor 8 and opening 21 are located in the aorta.

For system operation, proximal connections 16 and 20 leading to the thermistors are plugged into connections TH1 and TH2, respectively, of a small evaluating device 34 (FIG. 6) having two readout display panels 35 and 36. In the left hand display panel 35 the blood temperature can be read in Centigrade degrees. Alternatively the cardiac output HZV can be read after switch over key U is pressed at 37.

If the hydrostatic blood pressure is measured via lumina 6 and 21, corresponding connections 13, 23 can be plugged into plugs P1 and P2 in evaluating device 34. In the right hand display panel 36 the blood pressure P, the pressure gradient P, the systolic discharge amount SAM and the area KOF of the valve opening can be displayed in response to U switch over key 38. Also provided is E/A on off switch 39, calibrating keys Eich and T, 40, and a start key 41. Thus only the one catheter is required to perform a stenosis dilatation and to monitor its success.

To determine the cardiac output, a cryogen is injected into the left ventricle of the heart via connection 13 and channel, 3 and leaves through openings 6. Dilatation balloon 7 is not inflated in this case. Since openings 6 are arranged in the curved area PT of the distal end, the cryogen is swirled thoroughly in the blood, which is then pumped by the cardiac activity through aortic valve 33 and flows past thermistor 8. The temperature curve at this thermistor over time is shown as T1 in FIG. 5. The vertical arrow on the time axis t represents the beginning of the injection. At this beginning, start key 41 may be pressed. One can see that the temperature drops relatively quickly. This is first due to the fact that the cryogen in catheter tube 2 already flows past thermistor 8 in the aorta before leaving openings 6. The temperature drop is dependent on the absolute blood temperature, the amount of injected cryogen, the thermal insulation between channel 3 and thermistor 8 and the blood circulation. The measured temperature curve in the dropping area of curve T1 is a superposition of the primary cooling of the thermistor 8 when the cryogen flows through the catheter, and a further cooling triggered after a certain time by the recirculation of the blood from opening 6 into the aorta. The shape of the curve, for example the initial temperature drop and the new increase, already allows conclusions to be drawn on the cardiac output if the evaluating device is calibrated accordingly with the aid of calibrating keys 40.

A further possibility is to record the temperature curve at second thermistor 17, as shown by the dotted line T2 in FIG. 5. This thermistor 17 also is cooled by the cryogen flowing past it in catheter tube 2, at a later time than in the case of the first encountered thermistor 8. The cooling also takes place faster, and the lowest temperature is lower than with the first thermistor 8. This is due to the fact that this second thermistor 17 is located in the immediate vicinity of openings 6 where the cryogen flows out and is pumped toward the aortic valve, again flowing directly past thermistor 17. This temperature curve T2 thus also is due to a superposition of two cooling effects. Since the blood mixed with the cryogen is transported off toward the aortic valve relatively quickly, the temperature rises at second thermistor 17 faster. The differential areas between the two temperature curves T1 and T2 shown by the hatching in FIG. 5 also can be evaluated with respect to the cardiac output in evaluating device 34.

The pre- and post- stenotic blood pressure and the pressure gradient are known from the hydrostatic pressure measurement over openings 6 and 21. From the stated values, namely the cardiac output, the systolic discharge time and the pressure gradient, and from these values the area of the opening of the aortic valve 33, the evaluating device calculates with the aid of known formulae and displays the various readings.

If the aortic valve is constricted, then dilatation balloon 7 is inflated and the stenosis thereby burst open and distended. By subsequent measurement of the pre- and post- stenotic blood pressure and the pressure gradient and cardiac output, it can be ascertained immediately after this dilating measure whether aortic valve 33 has already been sufficiently distended. If this is not the case, dilatation balloon 7 is again inflated further and the resulting new distention quickly checked by new measurements.

The described catheter 1 can also be used alone for diagnostic purposes in the conventional manner, in particular when it is provided with a further opening 21 and a further temperature sensor 17. This also insures the universal use of the same catheter for dilatation purposes and for determining the cardiac output in the anterograde direction on the pulmonary valve, tricuspid valve and mitral valve.

In a healthy person with a tightly closing aortic valve, no temperature drop is measured at thermistor 18 located in the ventricle after a cryogen solution is injected through opening 21. If a temperature drop occurs there nevertheless, this is evidence of valvular insufficiency. The degree of insufficiency can be increased in particular if the valve is burst open. By antegrade injection of a cryogen solution before and after the valve is burst open, the insufficiency can be calculated and the anterograde cardiac volume thereby corrected.

As shown hereinbefore, this invention has provided comprehensive instrumentation that is for the first time able to quickly and efficiently conduct a diagnosis of the cardiovascular system of a patient with a single placement of a novel catheter structure in the left heart. For example, analysis and treatment of a stenosis is now made possible with a single catheter insertion.

At this stage of the art, as seen from herein referenced prior art for example, the automated processing of medical data with programmable computer data processing systems is routine, and such systems process data from catheter sensors to determine cardiac output and other critical data representative of the state of a patient's cardio-vascular system. The implementation of this invention with such data processing systems is illustrated in the block system diagram of FIG. 7. As may be seen from similar reference characters and catheter sensor notation, the computer system 34 inputs and manual controls have been heretofore described, together with the manner of processing data for critical analysis of the cardiac system. For example the determination of a stenosis area about a cardiac valve is known by use of Gorlin's formula.

Figure 7:
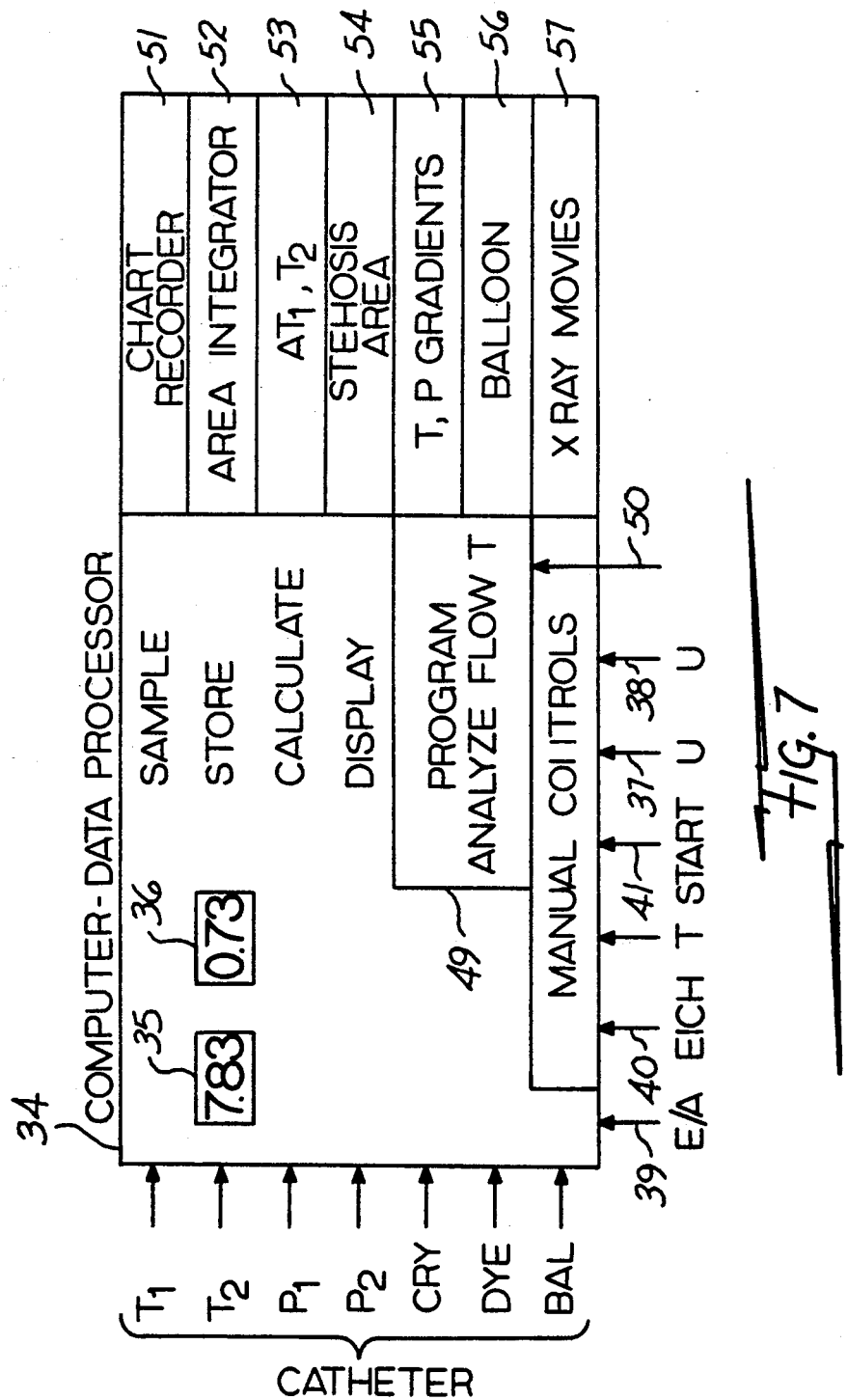
FIG. 7 is a block system diagram of instrumentation operable in accordance with this invention in the diagnosis of cardiac conditions.

With specific reference to FIG. 7, it is seen that a suitable program 49 for instrumentation 34 incorporating a general purpose computer may be manually prepared and entered at 50. Thus, any modifications of the calculation techniques necessitated by the unique flow conditions of cooling fluids in two directions past the temperature sensors provided by this invention for example are programmed by those skilled in such arts, as indicated by the terminology "analyze flow T".

Other features of the comprehensive instrumentation made possible by this invention are indicated by block system features at the right hand portion of this figure. Thus a chart recorder 51 displaying the waveforms of FIG. 5 provides instrumentation for analysis of temperature gradients, overlaps and areas, from which cardiac volume is determined. Also this provides a time scale and evidence of the injection rate and start time to assure that the analysis is proper when the cryogen impulse is manually released. This can supplement or replace the digital readouts 35, 36, produced by computer calculation by selecting on the time scale of the impulse period a critical area of the lowered temperature reading for integrating the area to provide a cardiac output reading in properly designated units of measurement, as performed in block 52.

Similarly in block 53, the system compares two different temperatures T1 and T2 for differences to produce data that permits diagnosis of valves, stenosis and the like. Similarly the stenosis or valve area designated in block 54 is ascertained from the pressure sensors P1, P2 of the catheter and processed for example by Gorlin's formula.

Temperature or pressure gradients may be processed and digitally displayed by means of the system represented in block 55. For treatment of data relating to the balloon, which may be inflated to a particular pressure for example to treat a stenosis, the system of block 56 is provided.

Also for the purpose of complete diagnosis and analysis of heart damage following an infarction for example, the dye injection technique using the catheter lumina may be used in conjunction with XRay movies 57.

It is therefore seen that a comprehensive examination and treatment of a cardiac patient is attainable by means of this invention more efficiently in time lapse, which may be critical, and with much less uncomfort and risk to the patient with the single multi-purpose catheter and accompanying instrumentation of this invention. Thus, improved diagnostic and treatment techniques for cardiac patients are made possible.

I claim:

1. Instrumentation for determining cardiac output by means of a single catheter introduced along an aorta to extend into the left heart by measurement of the change of temperature resulting from the injection, comprising in combination: distal cryogen discharge means positioned on the catheter for entering a cryogen impulse into the bloodstream of the left ventricle,
a temperature sensor disposed within the catheter toward a proximal position from the cryogen discharge position for positioning in the aorta having accompanying temperature processing means for sensing temperature changes at the temperature sensor position over a cooling-warming cycle generated by said cryogen impulse to establish temperature changes effected in the bloodstream of the aorta introduced by both flow of cryogen through the catheter past the sensor before entering the bloodstream and flow of chilled blood toward the aorta past the single sensor in response to the injection of the cryogen impulse.

2. The instrumentation defined in claim 1 further characterized by:
analyzing means for processing the temperature changes sensed by said sensor and displaying indicia therefrom representative of the cardiac output.

3. The instrumentation defined in claim 2 further characterized in that the analyzing means responds to an impulse injection of cryogen to determine over a blood cooling interval sensed temperature response to both the initial change of temperature from the cryogen flow and the subsequent change of temperature from the flow of cooled blood.

4. The instrumentation defined in claim 2 further characterized by:
cardiac output calculating means for determining the cardiac output from the integration of the sensed temperature decrease over a selected time period during the blood cooling interval.

5. The instrumentation defined in claim 3 further characterized by:
cardiac output calculating means for determining the cardiac output from the temperature gradient response sensed in response to a said impulse injection of cryogen.

6. Instrumentation for determining cardiac output from a catheter when introduced into the left heart by measurement of the change of temperature resulting from the injection through a distal cryogen discharge position on the catheter of a cryogen into the bloodstream of the cardio vascular system, comprising in combination:
a temperature sensor disposed within the catheter toward a proximal position from the cryogen discharge position and adapted for sensing temperature changes both from the flow of cryogen through the catheter past the sensor before entering the bloodstream and from the flow of chilled blood past the sensor following the injection of the cryogen, and
means including two temperature sensors located at different positions within the catheter for processing the temperature changes detected on opposite sides of the aortic valve to determine therefrom a measure of valvular sufficiency.

7. The instrumentation defined in claim 6 further characterized by a catheter having two of said temperature sensors located in the catheter for positioning on opposite sides of the aortic valve and further including means for injecting cryogen on either side of the valve.

8. Instrumentation for determining cardiac output from a catheter when introduced into the left heart by measurement of the change of temperature resulting from the injection through a distal cryogen discharge position on the catheter of a cryogen into the bloodstream of the cardio vascular system, comprising in combination:
a temperature sensor disposed within the catheter toward a proximal position from the cryogen discharge position and adapted for sensing temperature changes both from the flow of cryogen through the catheter past the sensor before entering the bloodstream and from the flow of chilled blood past the sensor following the injection of the cryogen further comprising dilatation balloon structure located on the catheter for positioning in the aortic valve and temperature sensitive instruments positioned on both sides of the balloon structure.

9. The instrumentation defined in claim 1 further characterized by pressure sensing means located at two positions along the catheter positionable for measuring the blood pressure on opposite sides of the aortic valve when the catheter is moved into the left ventricle.

10. The instrumentation defined in claim 1 further comprising the location of a further temperature sensor disposed near the distal end (PT) of the catheter for positioning within the heart.

11. The instrumentation defined in claim 1 further characterized by the location of two spaced said temperature sensors along the length of the catheter.

12. The instrumentation defined in claim 1 further characterized by a plurality of sensors comprising both temperature and pressure sensors located in the catheter adapted to determine a plurality of physical conditions of the vascular-cardio system of a patient from a single location of the catheter in the left heart.

13. The instrumentation defined in claim 12 further characterized by means for analyzing data sensed by one or more of said sensors in the catheter at a single catheter location to determine the presence of stenosis.

14. Instrumentation for determining cardiac output from a catheter when introduced into the left heart by measurement of the change of temperature resulting from the injection through a distal cryogen discharge position on the catheter of a cryogen impulse into the bloodstream of the cardio vascular system, comprising in combination:
a temperature sensor disposed within the catheter toward a proximal position from the cryogen discharge position and adapted for sensing temperature changes both from the flow of cryogen through the catheter past the sensor before entering the bloodstream and from the flow of chilled blood past the sensor following the injection of the cryogen, pressure gradient determining sensors in the catheter positionable on opposite sides of a stenosis, and calculating means responsive to the catheter sensors for determining the area of the stenotic opening.

15. In the method of determining cardiac output from a single catheter introduced into the left side of the arterial cardiovascular system by measurement of the change of temperature resulting from the injection of a cryogen solution into the bloodstream of said cardiovascular system, the improvement comprising:

sensing the temperature from a single temperature sensor disposed within the catheter toward a proximal position from the cryogen injection location during a time period that the temperature is being changed by flow of the cryogen solution being discharged from a distal end of the catheter into the blood to determine over a cooling and warming period responsive to an impulse injection of a cryogen both the cooling due to the flow of the cryogen solution through the catheter and the cooling from the returning blood flowing back toward the temperature sensor.

16. The method of claim 15 further comprising the step of:

analyzing the sensed temperature at said sensor over a predetermined time period within said cooling period to determine cardiac conditions.

17. The method of claim 15 including the step of disposing the temperature sensor proximally within the catheter, and positioning the sensor within the aorta. positioning the sensor within the aorta.

18. The method of claim 15 including the step of disposing the temperature sensor within the left ventricle.

19. In the method of determining cardiac output from a catheter introduced into the left heart by measurement of the change of temperature resulting from the injection of a cryogen solution, the improvement comprising:

sensing the temperature from a single temperature sensor disposed within the catheter in the left heart during a time period that the temperature is being changed by flow of a cryogen solution being discharged from the distal end of the catheter into the blood to determine over a cooling period responsive to an impulse injection of a cryogen both the cooling due to the flow of the cryogen solution through the catheter and the cooling from the returning blood flowing back toward the temperature sensor, disposing a second temperature sensor within the catheter at a position within the aorta, and producing from the temperatures of both sensors in response to the cryogen solution data indicative of the cardiac condition of a patient.

20. The method of diagnosing a plurality of cardiac conditions from a single insertion of a catheter into the left heart, comprising the steps of:

determining the temperature within the aorta, and determining the pressure differential on opposite sides of the aortic valve.

21. The method of diagnosing plurality of cardiac conditions from a single insertion of a catheter into the left heart, comprising the steps of:

determining the temperature within the aorta, determining the pressure differential on opposite sides of the aortic valve, and determining from the temperature and pressure differential the area of the aortic valve.

22. The method of gathering data, diagnosing and treatment of a stenosis in the cardiac system of a patient with the single insertion of a catheter into a resident position in the left heart comprising the steps of:

sensing cardiac output by the thermal dilution technique from discharge of a cryogen at a distal end of the catheter and sensing of temperature from a sensor located toward the proximal end of the catheter, sensing at different locations along the length of said catheter injected in the cardiac system the flow conditions of blood to determine the presence of a stenosis, and dilating the stenosis by means of a balloon located on the catheter between said different locations.

* * * * *